(12) United States Patent
Venugopalan et al.

(10) Patent No.: US 9,569,906 B2
(45) Date of Patent: Feb. 14, 2017

(54) PCDA-PHBV ELECTROSPUN ADHERENT MATS AS AUTHENTICATION FEATURE

(71) Applicant: COUNCIL OF SCIENTIFIC AND INDUSTRIAL RESEARCH, New Delhi (IN)

(72) Inventors: Premnath Venugopalan, Pune (IN); Jyoti Prakash Jog, Pune (IN); Sachin Dubey, Pune (IN); Usman Khan, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/908,871

(22) PCT Filed: Jul. 31, 2014

(86) PCT No.: PCT/IN2014/000503
§ 371 (c)(1),
(2) Date: Jan. 29, 2016

(87) PCT Pub. No.: WO2015/015515
PCT Pub. Date: Feb. 5, 2015

(65) Prior Publication Data
US 2016/0180625 A1    Jun. 23, 2016

(30) Foreign Application Priority Data

Jul. 31, 2013   (IN) .......................... 2290/DEL/2013

(51) Int. Cl.
*G01N 31/22* (2006.01)
*G07D 7/12* (2016.01)
(Continued)

(52) U.S. Cl.
CPC ............... *G07D 7/122* (2013.01); *A24D 1/02* (2013.01); *D01D 1/02* (2013.01); *D01D 5/003* (2013.01);
(Continued)

(58) Field of Classification Search
CPC ........... A24D 1/02; D01D 1/02; D01D 5/003; D01F 1/10; D01F 6/84; D10B 2331/04; G01N 21/78; G01N 31/22; G07D 7/00; G07D 7/12; G07D 7/122; G07D 7/14
See application file for complete search history.

(56) References Cited

U.S. PATENT DOCUMENTS

| | | | |
|---|---|---|---|
| 6,468,759 B1 * | 10/2002 | Charych | ............... B82Y 30/00 435/183 |
| 2005/0037498 A1 * | 2/2005 | Ribi | ................... G01N 31/229 436/2 |
| 2012/0160255 A1 | 6/2012 | Ghanavi | |

FOREIGN PATENT DOCUMENTS

| FR | 2763080 A1 | 11/1998 |
|---|---|---|
| WO | 2005025258 A2 | 3/2005 |
| WO | 2010-112940 A1 | 10/2010 |

OTHER PUBLICATIONS

International Search Report in PCT/IN2014/000503, mailed Feb. 6, 2015.

* cited by examiner

*Primary Examiner* — Jennifer Wecker
(74) *Attorney, Agent, or Firm* — Andrews Kurth Kenyon LLP

(57) ABSTRACT

The present invention discloses the adherent PHBV-PCDA electrospun mats on paper for use as an authentication feature. Further disclosed herein is the process for preparation of adherent PHBV-PCDA electrospun mats and use of the above product to authenticate cigarettes.

10 Claims, 7 Drawing Sheets

(51) Int. Cl.
    *G01N 21/78*    (2006.01)
    *D01D 5/00*     (2006.01)
    *A24D 1/02*     (2006.01)
    *G07D 7/00*     (2016.01)
    *G07D 7/14*     (2006.01)
    *D01F 1/10*     (2006.01)
    *D01F 6/84*     (2006.01)
    *D01D 1/02*     (2006.01)
    *G01N 33/543*   (2006.01)

(52) U.S. Cl.
    CPC . *D01F 1/10* (2013.01); *D01F 6/84* (2013.01);
        *G01N 21/78* (2013.01); *G07D 7/00* (2013.01);
        *G07D 7/12* (2013.01); *G07D 7/14* (2013.01);
        *D10B 2331/04* (2013.01); *G01N 31/22* (2013.01)

| Solvent | Before exposure | After exposure |
|---|---|---|
| Chloroform | CHLOROFORM R value=60 | CHLOROFORM R value avg=133 |
| Dichloromethane | DMF R value=60 | DMF R value avg=177 |
| Xylene | XYLENE R value=60 | XYLENE R value avg=141 |
| Tetrahydrofuran(THF) | THF R value=60 | THF R value avg=191 |
| Ethanol | ETHANOL R value=60 | ETHANOL R value avg=167 |

Figure 9

PCDA-PHBV ELECTROSPUN ADHERENT MATS AS AUTHENTICATION FEATURE

FIELD OF THE INVENTION

Present invention relates to the PCDA-PHBV electrospun adherent mats on paper for use as an authentication feature. Particularly, present invention relates to preparation of adherent PHBV-PCDA electrospun mats and use of the above product to authenticate cigarettes.

BACKGROUND AND PRIOR ART OF THE INVENTION

Authentication of documents, currency notes, certificates and detections of counterfeiting using simple means without need for extensive interventions is a challenge that is being addressed by many technologists and scientists. In some products, this feature is provided for, but still does not solve the issue of counterfeiting, for eg as in cigarettes it is provided for a pack, but is not an essential feature of each cigarette.

Fake cigarettes are a major problem for cigarette manufactures across the globe as the cigarette counterfeiting is immensely lucrative, with profits easily rivaling those of the narcotics trade. The trade in counterfeit cigarettes has been a problem for years and it is a growing global problem that hurts tobacco manufacturers to the tune of hundreds of millions of dollars each year. In addition to deceiving smokers into buying fake cigarettes, the trade in counterfeit cigarettes supports organized crime. Also, counterfeited cigarettes are often of substandard quality and do not comply with government and industry standards. Since these cigarettes are manufactured using contaminated tobacco leaves; the use of the same results in increased health risks associated with smoking. Thus counterfeited cigarettes very often contaminated with much higher levels of tar, nicotine, carbon monoxide, lead, cadmium, and arsenic than genuine brand-name cigarettes. Also, consumers buy fake cigarettes that are transported and stored in unhygienic conditions.

Fake cigarettes represent a billion-dollar industry across the globe and with tobacco taxes rising aggressively, fake cigarettes also grown in popularity as the same is available at a lesser price. Since the consumer intend to save few dollars on their smokes, the smokers are ignorant of counterfeiting cigarettes and the price becomes more relevant than the harmful additives, which normally included in the fake cigarettes like feces and sawdust that are even worse than that of a normal cigarette.

Thus the fake cigarettes become a global challenge not only for the manufacturers but also on the governments due to substantial increase in health risks.

Detecting illegal cigarettes using portable E-noses based on the differences between odors from counterfeit and genuine cigarettes is disclosed in article titled "Cigarette Brand Identification Using Intelligent Electronic Noses" by Dehan Luo. However, the method is tedious and non-reliable.

In the light of the foregoing, there is a need in the art to provide an effective solution that can take care of counterfeiting in individual cigarettes but not on the cigarette packets.

Also, premier cigarettes need a feature to authenticate their originality by the end user himself. Moreover the features available today cannot authenticate individual cigarette, rather they authenticate only the boxes containing them.

There is therefore a need for counterfeiting and authentication features which can be visibly observed. Most features available today are on the packet and not on individual cigarette. The current available solutions for counterfeiting and authentication include holographic stickers, fluorescent inks, screen printing, offset printing, flexographic printing and blind embossing. Again, all these features are marked on the packet of cigarette and not on the individual cigarette. Further, these features are costlier and difficult to use and also vests with issues such as biodegradability and safety.

So there is a need to provide means to detect counterfeiting in cigarettes that will enable detection in each unit, rather for an entire pack. Also, the solution proposed should be such that it does not affect the product itself during incorporation or detection, either in terms of aesthetics or in terms of method of use. The feature and method should also be such that it preferably provides a simple visual means of detection of counterfeiting.

OBJECTS OF THE INVENTION

Main object of the present invention is to provide PCDA-PHBV electrospun adherent mats on substrate for use as an authentication feature.

Another object of the invention is to provide PCDA-PHBV electrospun adherent mats on paper for use as an authentication feature to individual cigarette, which may be readily detectable.

Yet another object of the invention is to provide a process of preparation of PCDA-PHBV electrospun adherent mats on substrate.

Yet another objective of the invention is to provide a method of detection of counterfeiting of cigarettes.

SUMMARY OF THE INVENTION

Accordingly, present invention provides an electrospun nanofiber adherent mats comprising 60 to 90% Polyhydroxybutyrate-co-valerate (PHBV) and 10 to 40% 10,12-Pentacosadiynoic acid (PCDA) deposited on a substrate wherein said mats are useful in detecting counterfeiting in a substrate.

In an embodiment of the present invention, the mats may optionally contain 0.25 to 2% nano particles of a metal oxide preferably zinc oxide.

In an embodiment, present invention provides a process for preparation of electrospun nanofiber adherent mats comprising the steps of:
 a. sonicating a supersaturated solution of 10,12-Pentacosadiynoic acid (PCDA) in chloroform for period in the range of 25 to 30 min followed by extruding the using PTFE syringe filter to obtain a solution;
 b. stirring the solution of copolymer polyhydroxybutyrate-co-valerate (PHBV) in dichlorobenzene for period in the range of 5 to 6 hr;
 c. mixing the solution as obtained in step (a) with solution of copolymer polyhydroxybutyrate-co-valerate (PHBV) as obtained in step (b) in the ratio ranging between 1:9 to 4:6 followed by stirring for period in the range of 50 to 60 minute to obtain a solution;
 d. depositing the mixture on a substrate by applying 15 kV potential at a distance of 10 to 15 cm between a syringe and a collector wherein the syringe contains a solution as obtained in step (c) to obtain electrospun nanofiber adherent mats.

In yet another embodiment of the present invention, the process optionally includes a step of mixing sonicated homogenous solution of metal oxide preferably zinc oxide in chloroform to the PCDA solution of step (a) prior to mixing with PHBV solution.

In yet another embodiment of the present invention, the substrate is pasted on collector and substrate is selected from the group consisting of paper, metal, sticker and glass and the collector is an aluminum sheet.

In yet another embodiment, present invention provides a method of detecting counterfeit in a substrate comprising:
a) providing electrospun nano fiber adherent mats as claimed in claim 1 on the substrate; and
b) observing the colour change in the electrospun nanofiber adherent mat induced by a stimulus to detect counterfeit.

In yet another embodiment of the present invention, the stimulus is selected from the group consisting of temperature, solvent, pressure or UV.

In yet another embodiment of the present invention, the colour change in the mats is irreversible or reversible.

In yet another embodiment of the present invention, the colour changes in the mats with Zinc oxide nano particles is reversible.

In yet another embodiment, present invention provides a method of detecting the purity of organic solvents comprising exposing the electrospun nanofiber adherent mats of Polyhydroxybutyrate-co-valerate (PHBV) and 10,12-Pentacosadiynoic acid (PCDA) to the solvent and assessing the purity based on the differential colour change and a different red value observed.

BRIEF DESCRIPTION OF THE DRAWINGS

FIG. 9 represents irreversible color change on exposure of PCDA-PHBV fibers to solvents, showing a differential color change and a different red value after exposure.

DETAILED DESCRIPTION OF THE INVENTION

Figure 1:
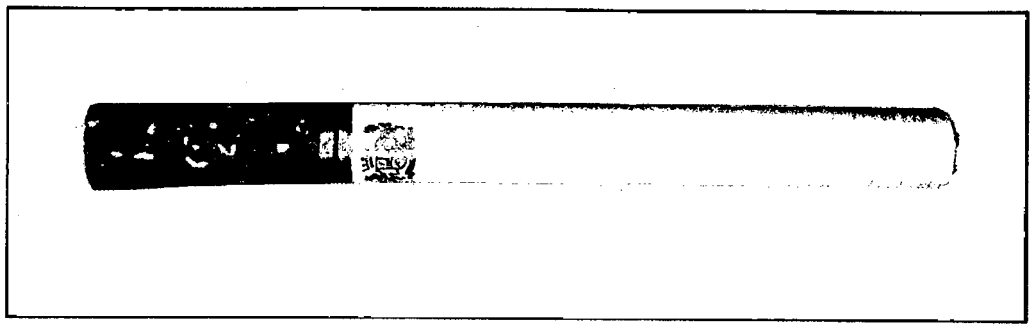
FIG. 1 represents ITC branded Classic cigarette as sold in market, having electrospun nanofibers of PHBV-PCDA on it, in the monomeric form. They are white in color and cannot be seen.

Accordingly, present invention provides electrospun nanofiber adherent mats composed of polymers selected from Polyhydroxybutyrate-co-valerate (PHBV) (88% Polyhydroxybutyrate and 12% valerate) and 10,12-Pentacosadiynoic acid (PCDA) for detecting counterfeiting in a substrate. The electrospun nanofiber adherent mats further optionally contain nanoparticles of a metal oxide, preferably being Zinc Oxide. The electrospun nanofiber adherent mats according to the invention can be directly deposited on a substrate as an authentication feature for detection of counterfeiting in cigarettes and can directly deposit on the rolling paper of cigarette and various other surfaces to provide a feature/indicator that can change color to a stimulus. The substrate according to the invention may be selected from paper, metal, sticker, plastic etc. The invention provides an authentication feature for detection of counterfeiting in cigarettes, wherein each cigarette is provided with said feature.

The electrospun nanofiber adherent mats extending in two dimensions and having limited thickness in a third dimension, wherein, limited thickness ranging from micro meters to nanometers, prepared by electro spinning process. The size of the electrospun nanofiber adherent mats of the instant invention is application-specific.

The mats comprise nanofibers that form a "network" of fibers and thus have substantial structural integrity and resilience, such that they may be reversibly stretched, compressed, bent or folded.

The invention discloses electrospun nanofiber adherent mats of polymers that changes color owing to the temperature change by exposing the fiber area to match stick, such that the mats may be deposited on a matrix to detect counterfeiting by visual means. The colour change may be reversible or irreversible.

The invention provides a process for preparation of electrospun nanofiber adherent mats of Polyhydroxybutyrate-co-valerate (PHBV) and 10,12-Pentacosadiynoic acid (PCDA) on a substrate as an authenticating feature, which comprises:
a) preparing monomer solution of 10,12-Pentacosadiynoic acid by sonicating 10,12-Pentacosadiynoic acid (PCDA) in chloroform, followed by extruding the solution using PTFE syringe filter;
b) optionally mixing the Sonicated homogenous solution of zinc oxide in chloroform to the PCDA solution of step (a);
c) mixing the solution of step (b) with solution of polyhydroxybutyratecopolymer with valerate (PHBV); and
d) electrospinning of the mixture followed by depositing the mixture on a substrate to obtain electrospun nanofiber adherent mats.

The invention provides a process of depositing electrospun nanofiber adherent mats made of Polyhydroxybutyrate-co-valerate (PHBV) and 10,12-Pentacosadiynoic acid (PCDA) on a substrate which comprises:
i. applying 15 kV potential at a distance of 10 to 15 cm between a syringe and a collector, wherein the syringe contains a solution of mixture containing PHBV-PCDA and optionally Zinc Oxide and the substrate is pasted on aluminium collector, to obtain adherent electrospun mats of PHBV-PCDA deposited on the substrate.

The substrate pasted on the collector may be selected from paper used to wrap the cigarette, metal, sticker and plastic.

The invention provides a method of detecting counterfeit in a substrate comprising:
  a) Providing electrospun nanofiber adherent mats of Polyhydroxybutyrate-co-valerate (PHBV) and 10,12-Pentacosadiynoic acid (PCDA) on the substrate; and
  b) Observing the colour change in the electrospun nanofiber adherent mat induced by a stimulus to detect counterfeit.

The stimulus is selected from the group consisting of temperature, solvent, pressure or UV and the colour change in the mats may be irreversible or reversible.

The colour change in the mats with Zinc oxide nano particles (45 nm) is reversible.

The invention provides a method of detecting counterfeit in a cigarette, said method comprising:
  a. providing electrospun nanofiber adherent mats of Polyhydroxybutyrate-co-valerate (PHBV) and 10,12-Pentacosadiynoic acid (PCDA) on cigarette paper; and
  b. observing the colour change in the electrospun nanofiber adherent mat induced by a stimulus to detect counterfeit.

The stimulus for the colour change in the electrospun nanofiber adherent mats may be selected from the group consisting of temperature, solvent, pressure or UV. Exposure to UV cannot bring blue to red color change, however, it will only polymerize PCDA from white monomeric form to blue polymerized state.

The colour change in the mats may be irreversible.

The mats further comprise Zinc oxide nano particles. The colour change in mats with ZnO nanoparticles is reversible, independent of the stimulus.

The electrospun nanofiber adherent mats made of PCDA-PHBV can be used to detect the purity of the solvents based on the differential colour change and a different red value by exposing the mats to solvents.

EXAMPLES

Following examples are given by way of illustration and therefore should not be construed to limit the scope of the invention.

Example 1

Preparation of Electrospun Nanofibers of Polyhydroxybutyrate-Co-Valerate (PHBV) and 10,12-Pentacosadiynoic Acid (PCDA) and their Direct Deposition on Rolling Paper and Tipping Paper A. Synthesis of Monomer of 10,12-Pentacosadiynoic Acid Into a 15 mL culture tube was added 0.5 grams of 10,12-Pentacosadiynoic acid obtained from Aldrich, USA. To this was added 3 ml of chloroform obtained from Rankem. The reaction mixture was sonicated for 30 minutes to get uniformity. This mixture was red in color. Using a 0.45 µm PTFE syringe filter, the solution was extruded to obtain a clear solution. The polymerized part was thus removed. This clear solution was added to a 100 ml round bottom flask and the chloroform was rotary evaporated to obtain 0.42 g of pure white monomer of 10, 12 Pentacosadiynoic acid.

B. Electrospinning of PHBV-PCDA-ZnO and Deposition of Nanofibers on Paper 1.76 g of 88% polyhydroxybutyrate copolymer with 12% valerate was added to 5 ml Dichlorobenzene in a 15 ml culture tube and allowed to stir for 6 hours. Into a 10 mL culture tube was added 0.02 g ZnO nanoparticles in 2 ml chloroform having average size of 45 nm obtained from Sigma-adlrich, USA. This solution was sonicated for 1 hour to obtain a homogenous solution. Simultaneously 0.20 g of monomerized 10,12-Pentacosadiynoic acid was added to 3 ml chloroform in a culture tube covered by aluminum foil. The solution was allowed to stir for 30 minutes. Soon after the ZnO solution was added to the PCDA solution to make up the total volume to 5 ml. The mixture was kept for stirring for another 1 hour. The PHBV solution after 6 hours was added to PCDA-ZnO solution mixture to make up the total volume to 10 ml making a 20 wt % solution. This mixture containing PHBV-PCDA-ZnO in a 15 ml culture tube was stirred for 1 hour. After 1 hour this solution was added to a 12 ml disposable syringe from dispovan. The needle was made blunt by rubbing on a coarse flint paper till the tapered tip was lost. This solution mixture in syringe was then fitted into a Harvard apparatus 11 plus syringe pump. The electrospinning collector was Aluminum plate with dimensions of an A4 paper. The cigarette was pasted on this aluminum collector using a scotch tape. A potential of 15 kV was applied between syringe and collector. The tip to collector distance was 15 cms and the flow rate was 1 ml/hour. Adhered electrospun fibers were obtained on cigarette paper on observation after 5 hours. The fibers were white in color and blended well with the paper on cigarette as shown in FIG. 1.

(C) Electrospinning of PHBV-PCDA-without ZnO and Deposition of Nanofibers on Paper 1.76 g of 88% polyhydroxybutyrate copolymer with 12% valerate was added to 5 ml Dichlorobenzene in a 15 ml culture tube and allowed to stir for 6 hours. Simultaneously 0.24 g of monomerized 10,12-Pentacosadiynoic acid was added to 5 ml chloroform in a culture tube covered by aluminum foil. The solution was allowed to stir for 30 minutes. The PHBV solution after 6 hours was added to PCDA-solution to make up the total volume to 10 ml making a 20 wt % solution. This mixture containing PHBV-PCDA-ZnO in a 15 ml culture tube was stirred for 1 hour. After 1 hour this solution was added to a 12 ml disposable syringe from dispovan. The needle was made blunt by rubbing on a coarse flint paper till the tapered tip was lost. This solution mixture in syringe was then fitted into a Harvard apparatus 11 plus syringe pump. The electrospinning collector was Aluminum plate with dimensions of an A4 paper. The cigarette was pasted on this aluminum collector using a scotch tape. A potential of 15 kV was applied between syringe and collector. The tip to collector distance was 15 cms and the flow rate was 1 ml/hour. Adhered electrospun fibers were obtained on cigarette paper on observation after 5 hours. The fibers were white in color and blended well with the paper on cigarette as shown in FIG. 1.

Example 2

Colour Change by Exposure to UV Indicating Counterfeit

Figure 2:
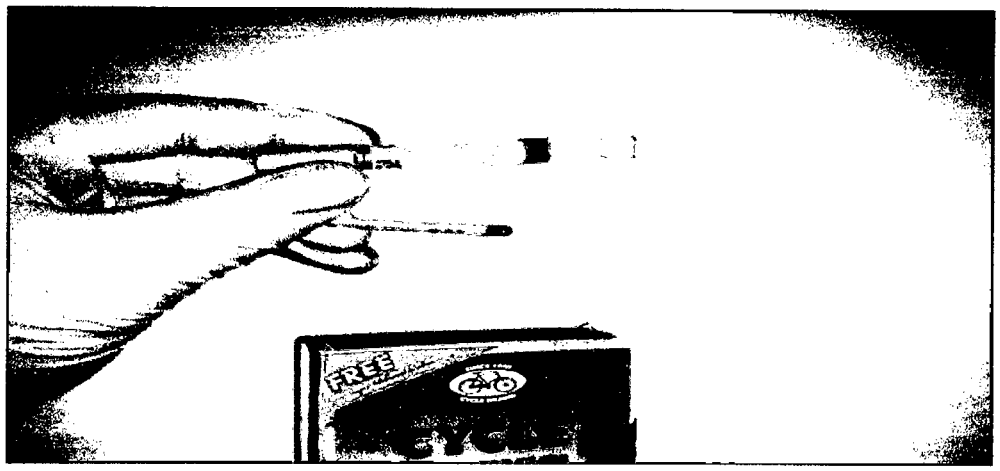
FIG. 2 represents the cigarette with blue band of nanofibers post polymerization by 254 nm shortwavelength UV radiation exposure for 30 seconds. The fibers are well adhered to the cigarette paper and do not wither upon rough handling also.

The cigarette paper having adhered electrospun nanofibers as prepared in example 1 was exposed to shortwave 254 nm UV radiation for 30 seconds. The white fibers turn blue due to polymerization by shortwave UV radiation as shown in FIG. 2.

Example 3

Colour Change by Heating Indicating Counterfeit

Figure 3:
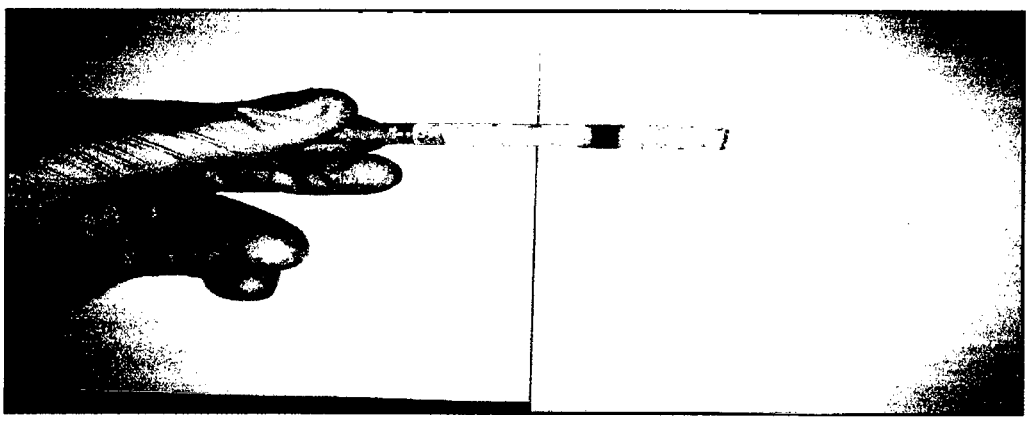
FIG. 3 represents the electrospun band of PHBV-PCDA nanofibers on cigarette turns red after heating with a matchstick from a distance of 10 cm. The stability of nanofibers is readily visible.

The cigarettes as prepared in example 1 were exposed to heating by matchstick from distances ranging 5-10 cms. The white fibers as obtained in example 1 were exposed to 254 nm UV radiation for 30 seconds to turn them blue. The blue fibers on the cigarette surface turned red upon receiving the heat and reverted back to blue upon removal of the matchstick as depicted in FIG. 3. This blue-red color transition was reproducibly obtained for 5 cycles.

Example 4

Deposition on Surface, Enumerating Affinity and Measuring the Adherence

Figure 4A:
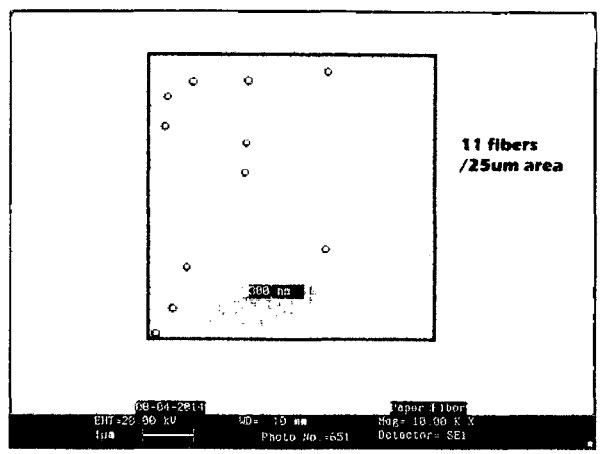
FIG. 4a-4c exhibit the SEM images of fiber of Cigarette paper as rough surface, Magic tap as Matt surface and Brown packaging tape as Glossy surface respectively.
Figure 4B:
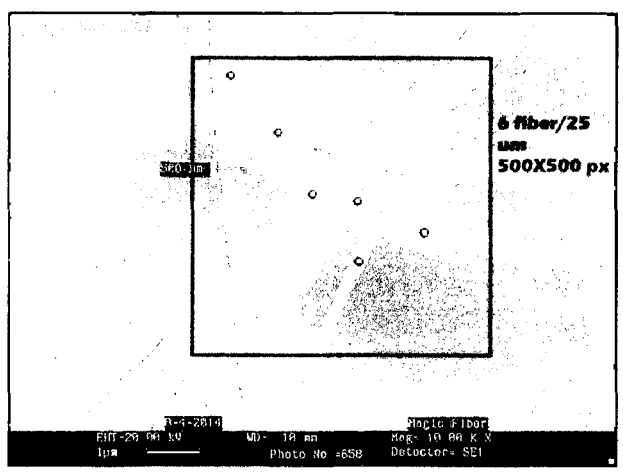
Figure 4C:
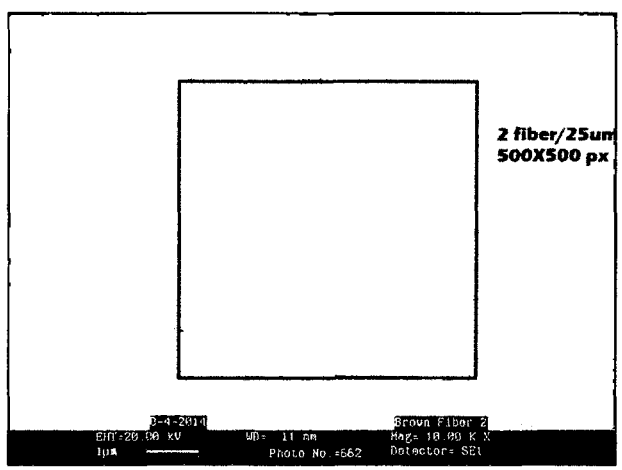

Three different surfaces were taken selected from cigarette paper as a rough surface; Magic tape as Matt surface and Brown packaging tape for Glossy finish surface and fibers were deposited. After the fibers were deposited SEM images were taken and the number of fibers counted in an area of 25 μm to enumerate the density and affinity of certain surfaces to attract more fibers compared to others as shown in below table 1 and FIG. 4a-4c.

TABLE 1

| Surface | Density Fibers/25 μm |
|---|---|
| Rough surface/Cigarette paper (FIG. 4a) | 0.44 |
| Matt/Magic tape (FIG. 4b) | 0.24 |
| Gloss/packaging brown tape (FIG. 4c) | 0.08 |

Figure 5A:
FIG. 5a-5c exhibit the SEM images after abrasion of fiber of Cigarette paper as rough surface, Magic tap as Matt surface and Brown packaging tape as Glossy surface respectively using the scotch tape (3M branded).
Figure 5B:
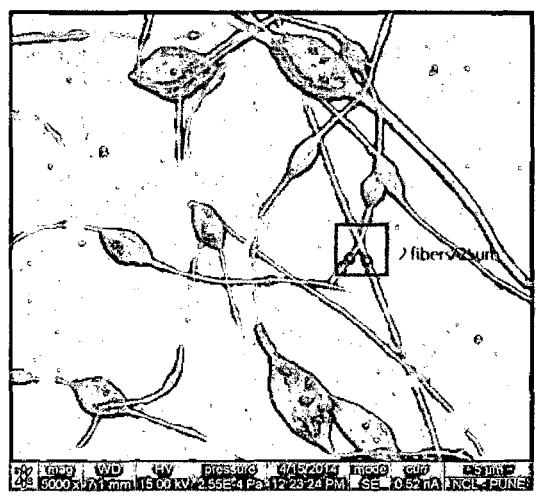
Figure 5C:
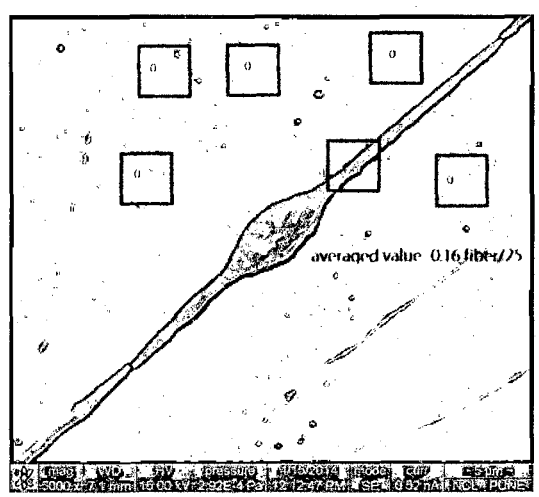

The density parameter clearly demonstrates that rough surface attracts more fibers compared to gloss finished surfaces, while matt finish surfaces falls in between them. All these surfaces were subject to same conditions of electrospinning (duration of deposition, flow rate, distance and voltage). Furthermore to demonstrate the adherence of fibers, the inventors have used abrasion using a scotch tape (3M branded) for removing the fibers from these surfaces. The scotch tape was stuck firmly on to these surfaces containing fibers and then removed slowly. To quantify the adherence, again performed SEM and determined the density, as depicted in table 2 and FIG. 5a-5c.

TABLE 2

| Surface | Density after abrasion | % abrasion |
|---|---|---|
| Cigarette/Rough finish | 0.32 | 27.27 |
| Matt surface | 0.08 | 66.6 |
| Glossy surface | 0.006 | 92.5 |

Figure 6A:
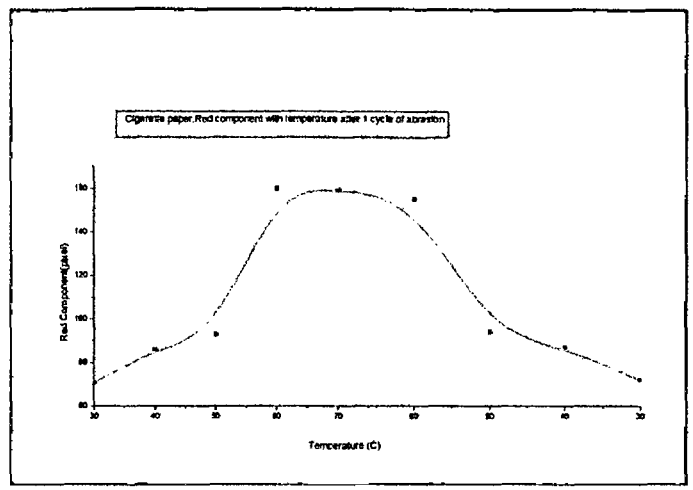
FIG. 6a-6c measuring the adherence from the colour changing abilities with temperature after abrasion of fiber of Cigarette paper as rough surface, Magic tap as Matt surface and Brown packaging tape as Glossy surface respectively using the scotch tape for 1 cycle.
Figure 6B:
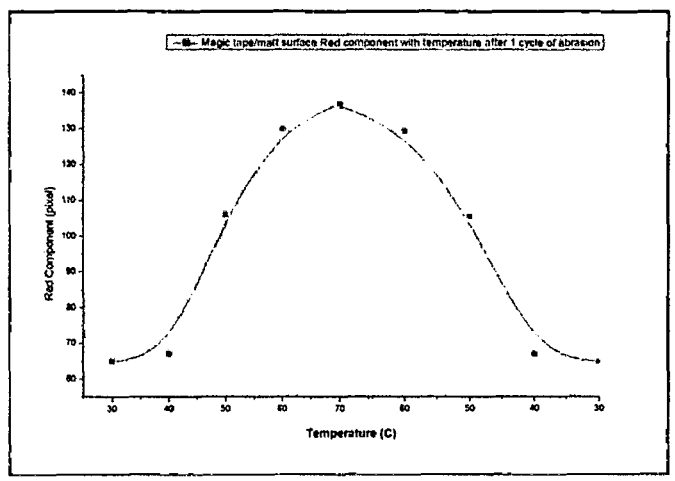
Figure 6C:
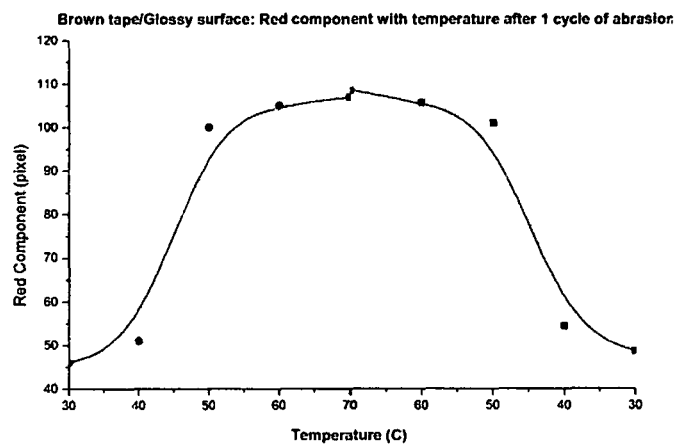

The invention provides measuring the adherence from the colour changing abilities of these surfaces after abrasion using the scotch tape for 1 cycle. The red color value has been measured using the color pick option in Paintbrush of windows 7. The RGB (Red green blue) value indicates the amount of Red based on the value of R and the R value was picked from the Paintbrush's tool, color pick. The results are shown below in table 3 and FIG. 6a-6c.

TABLE 3

| Surface | loss |
|---|---|
| 1. Cigarette/Rough surface | Only 3-5% loss in Red color value with temperatue |
| 2. Magic tape/Matt surface | Only 5% loss in Red color value with temperature |
| 3. Brown/glossy surface | 15% loss in Red color component after 1 cycle of abrasion. |

Example 5

Irreversible Color Change with Temperature

Figure 7A:
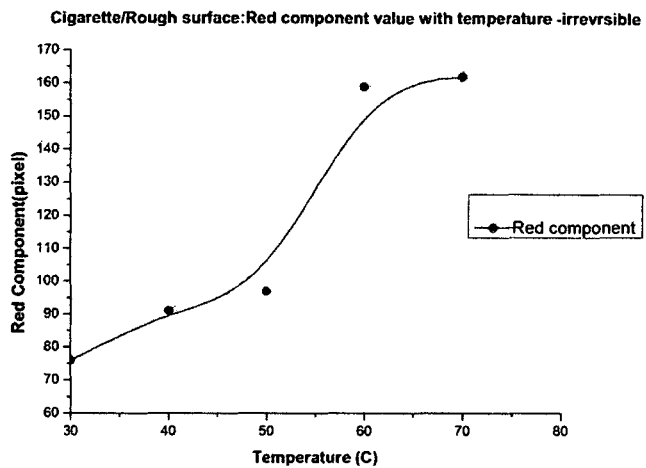
FIG. 7a-7c represents irreversible color change with temperature without ZnO nanoparticles for Cigarette paper as rough surface, Magic tap as Matt surface and Brown packaging tape as Glossy surface respectively.
Figure 7B:
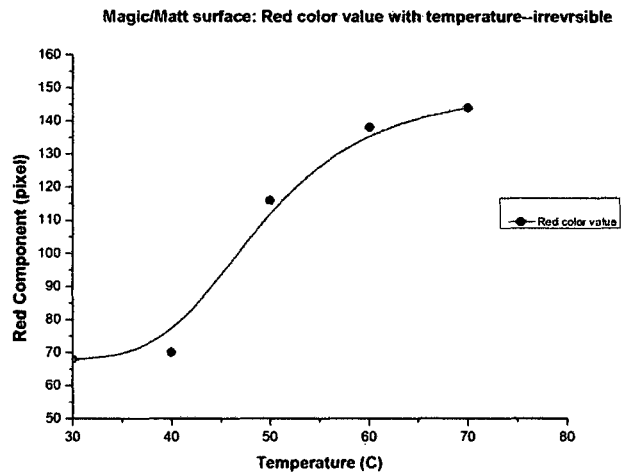
Figure 7C:
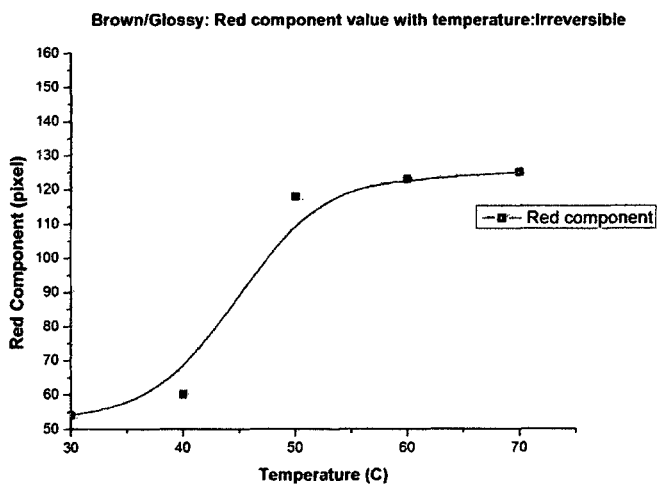

PCDA-PHBV electrospun mats that did not contain ZnO nanoparticles of 45 nm did not show reversibility in color even after single cycle of heating and cooling, as shown in FIG. 7a-7c.

Example 6

Reversible Color Change with Temperature

Figure 8A:
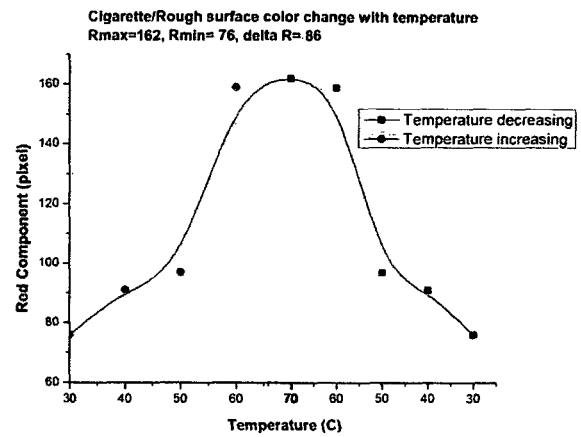
FIG. 8a-8c represents reversible color change for almost 5 cycles of heating and cooling up to 100° C. with PCDA-PHBV fibers made by doping with ZnO nanoparticles of 45 nm for Cigarette paper as rough surface, Magic tap as Matt surface and Brown packaging tape as Glossy surface respectively.
Figure 8B:
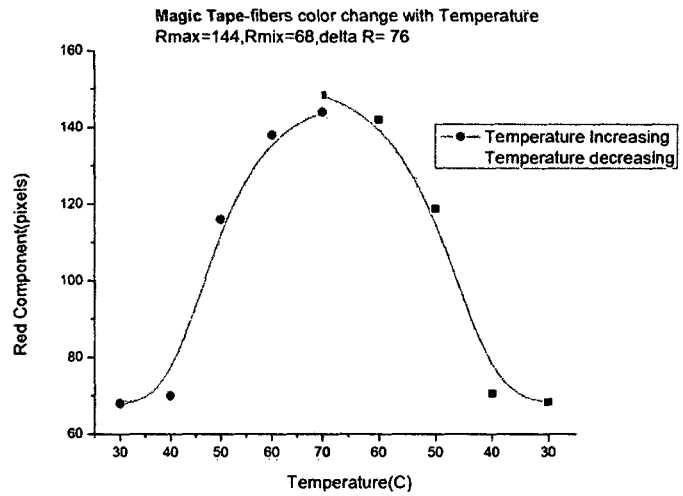
Figure 8C:
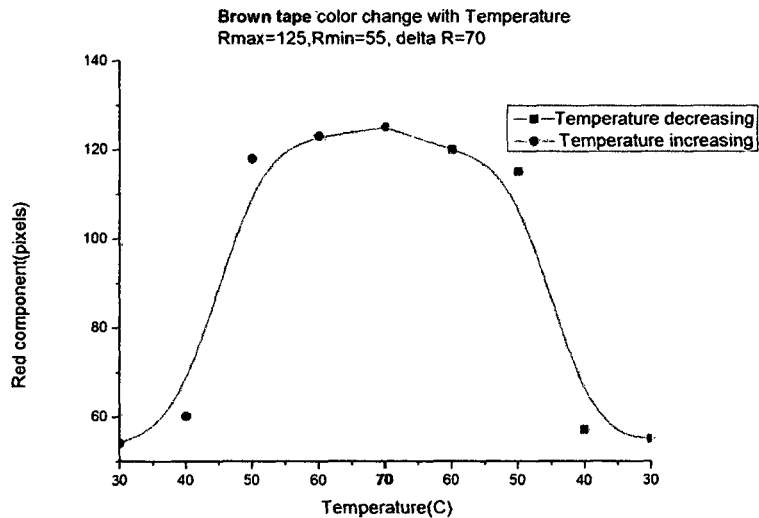

Reversible color change for almost 5 cycles of heating and cooling up to 100° C. were obtained when PCDA-PHBV fibers made by doping with ZnO nanoparticles of 45 nm obtained from Sigma-Aldrich. The results are depicted in FIG. 8a-8c.

Example 7

Irreversible Color Change on Exposure to Solvents

The PCDA-PHBV fibers were deposited on rough surface paper (whatmann filter paper no 1) and exposed to 0.1 ml of the solvents Chloroform, Dichloromethane, Xylene, Tetrahydrofuran (THF), Ethanol. They showed a differential color change and a different red value that could be used to decipher them. The results are depicted in FIG. 9.

The solvents were obtained from MERCK and were HPLC grade and proanalysi type. Ethanol used was absolute and analytical grade obtained from CHANGSU YANGYUAN Chemicals, CHINA.

5 data points were taken randomly on the pictures of these fibers to access their Red and Blue component via the color pick tool. The values obtained were then averaged to get a mean value which is shown here as R value avg. In both blue and Red fibers, where ever R value is mentioned, it is an average of 5 Red values.

ADVANTAGES OF THE INVENTION

Authentication feature may be included on each unit of item to be detected.
Simple visual means of detection.
Detection needs no additional infrastructure.
Reversible detection process.

We claim:
1. Electrospun nanofiber adherent mats comprising 60 to 90% Polyhydroxybutyrate-co-valerate (PHBV) and 10 to 40% 10,12-Pentacosadiynoic acid (PCDA) deposited on a substrate wherein said mats are configured for detecting counterfeiting in a substrate.
2. The electrospun nanofiber adherent mats as claimed in claim 1, wherein the mats may optionally contain 0.25 to 2% nano particles of a metal oxide preferably zinc oxide.

3. A process for preparation of electrospun nanofiber adherent mats comprising the steps of:
   a. sonicating a supersaturated solution of 10,12-Pentacosadiynoic acid (PCDA) in chloroform for a period of time in the range of 25 to 30 min, followed by extruding the solution using PTFE syringe filter to obtain a solution;
   b. stirring the solution of copolymer polyhydroxybutyrate-co-valerate (PHBV) in dichlorobenzene for a period of time in the range of 5 to 6 hr.;
   c. mixing the solution as obtained in step (a) with solution of copolymer polyhydroxybutyrate-co-valerate (PHBV) as obtained in step (b) in the ratio ranging between 1:9 to 4:6 followed by stirring for a period of time in the range of 50 to 60 minutes to obtain a solution;
   d. depositing the mixture on a substrate by applying 15 kV potential at a distance of 10 to 15 cm between a syringe and a collector wherein the syringe contains a solution as obtained in step (c) to obtain electrospun nanofiber adherent mats.

4. The process as claimed in claim 3, wherein the process optionally includes a step of mixing a sonicated homogenous solution of metal oxide preferably zinc oxide in chloroform to the PCDA solution of step (a) prior to mixing with PHBV solution.

5. The process according to claim 4, wherein the substrate is pasted on a collector and the substrate is selected from the group consisting of paper, metal, stick and glass and the collector is an aluminum sheet.

6. A method of detecting counterfeit in a substrate comprising:
   a) providing electrospun nanofiber adherent mats as claimed in claim 1 on the substrate; and
   b) observing the colour change in the electrospun nanofiber adherent mat induced by a stimulus to detect counterfeit.

7. The method according to claim 6, wherein the stimulus is selected from the group consisting of temperature, solvent, pressure or UV.

8. The method according to claim 6, wherein the colour change in the mats is irreversible or reversible.

9. The method according to claim 6, wherein the colour changes in the mats with Zinc oxide nano particles is reversible.

10. A method of detecting the purity of organic solvents comprising exposing electrospun nanofiber adherent mats of Polyhydroxybutyrate-co-valerate (PHBV) and 10,12-Pentacosadiynoic acid (PCDA) to the solvent and assessing the purity based on the differential colour change and a different red value observed.

* * * * *